United States Patent [19]

Vogt

[11] 4,112,098

[45] Sep. 5, 1978

[54] PYRAZOLO[1,5-C]QUINAZOLINE DERIVATIVES AND RELATED COMPOUNDS

[75] Inventor: B. Richard Vogt, Yardley, Pa.

[73] Assignee: E. R. Squibb & Sons, Inc., Princeton, N.J.

[21] Appl. No.: 842,718

[22] Filed: Oct. 17, 1977

[51] Int. Cl.² .............. A61K 31/415; A61K 31/505; C07D 487/04
[52] U.S. Cl. ................................ 424/251; 544/252
[58] Field of Search .............. 260/256.4F; 424/251

[56] References Cited

U.S. PATENT DOCUMENTS

| | | | |
|---|---|---|---|
| 3,171,740 | 3/1965 | Menzel et al. | 260/256.4 F |
| 3,313,815 | 4/1967 | Wolfe et al. | 260/256.4 F |
| 3,531,482 | 9/1970 | Ott | 260/256.4 F |

Primary Examiner—Donald G. Daus
Assistant Examiner—James H. Turnipseed
Attorney, Agent, or Firm—Lawrence S. Levinson; Merle J. Smith; Burton Rodney

[57] ABSTRACT

Compounds are provided having the structure

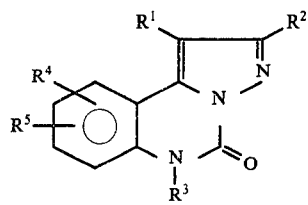

wherein $R^1$ is hydrogen, alkyl of 1 to 3 carbons, 1-(hydroxyimino)alkyl, alkanoylamino, amino, or

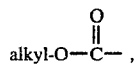

wherein alkyl in the above groups contains 1 to 4 carbons; $R^2$ is 1-(hydroxyimino)alkyl, alkanoylamino, amino,

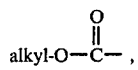

hydrogen, lower alkyl or phenyl (optionally substituted by $R^4$) wherein alkyl in the above groups contains 1 to 4 carbons; $R^3$ is hydrogen, lower alkyl, benzyl or phenyl (optionally substituted with $R^4$), dialkylaminoalkyl, hydroxyalkyl,

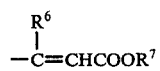

(wherein $R^6$ is hydrogen or alkyl, and $R^7$ is alkyl); with the proviso that $R^1$ or $R^2$ is 1-(hydroxyimino)alkyl, alkanoylamino or amino, when $R^3$ is hydrogen, lower alkyl, benzyl or phenyl; and $R^4$ and $R^5$ are the same or different and represent hydrogen, lower alkyl, lower alkoxy, alkanoyloxy, benzyloxy, hydroxy, halogen (Cl, Br and F), nitro and trifluoromethyl. The above compounds are useful as anti-allergy agents and antiinflammatory agents.

19 Claims, No Drawings

PYRAZOLO[1,5-c]QUINAZOLINE DERIVATIVES AND RELATED COMPOUNDS

The present invention relates to pyrazolo[1,5-c]-quinazoline derivatives of the structure

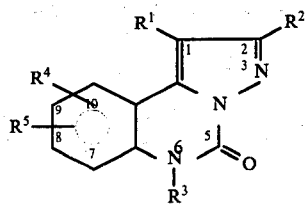

wherein $R^1$ is hydrogen, alkyl of 1 to 3 carbons, 1-(hydroxyimino)alkyl, alkanoylamino, amino, or

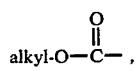

wherein alkyl in the above groups contains 1 to 4 carbons; $R^2$ is 1-(hydroxyimino)alkyl, alkanoylamino, amino,

hydrogen, lower alkyl or phenyl optionally substituted by $R^4$) wherein alkyl in the above groups contains 1 to 4 carbons;

$R^3$ is hydrogen, lower alkyl, benzyl or phenyl (optionally substituted by an $R^4$ radical as defined below), dialkylaminoalkyl, hydroxyalkyl,

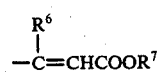

(wherein $R^6$ is hydrogen or alkyl, and $R^7$ is alkyl), with the proviso that $R^1$ or $R^2$ is 1-(hydroxyamino)alkyl, alkanoylamino, amino, when $R^3$ is hydrogen, lower alkyl, benzyl or phenyl;

$R^4$ and $R^5$ may be the same or different and are hydrogen, lower alkyl (1–4 carbons), lower alkoxy (1–4 carbons), hydroxy, alkanoyloxy (2–5 carbons),

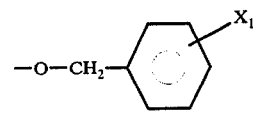

($X_1$ is hydrogen, lower alkoxy (1–4 carbons)), hydroxy, Cl, F, Br, $CF_3$ or $NO_2$.

Unless otherwise indicated the term "lower alkyl" or "alkyl" as employed herein includes both straight and branched chain radicals of up to eight carbon atoms, for instance, methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, and the like.

Unless otherwise indicated, the term "lower alkoxy" or "alkoxy" includes straight or branched chain radicals which correspond to the above lower alkyl groups attached to an oxygen atom.

Unless otherwise indicated, the term "lower alkanoyl" or "alkanoyl" as employed herein includes any of the above lower alkyl groups linked to a carbonyl group.

Unless otherwise indicated, the term "aryl" as employed herein contemplates monocyclic carbocyclic aryl radicals, for instance, phenyl and substituted phenyl radicals, such as lower alkyl phenyl (e.g., o-, m- or p-tolyl, ethylphenyl, butylphenyl, and the like), di(-lower alkyl)phenyl (e.g., 2,4-dimethylphenyl, 3,5-diethylphenyl, and the like), halophenyl, (e.g., chlorophenyl, bromophenyl, iodophenyl, fluorophenyl).

Preferred compounds encompassed by the structure of formula I include, but are not limited to, the following:

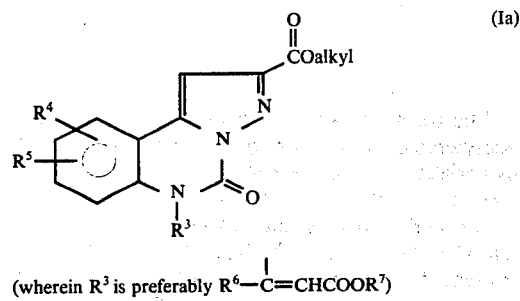

(wherein $R^3$ is preferably $R^6$—$\overset{|}{C}$=CHCOOR$^7$)

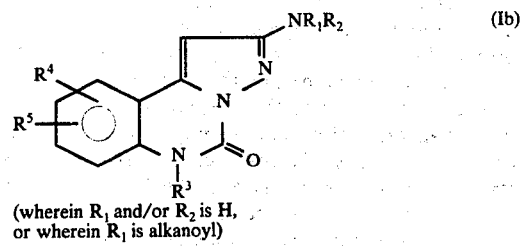

(wherein $R_1$ and/or $R_2$ is H, or wherein $R_1$ is alkanoyl)

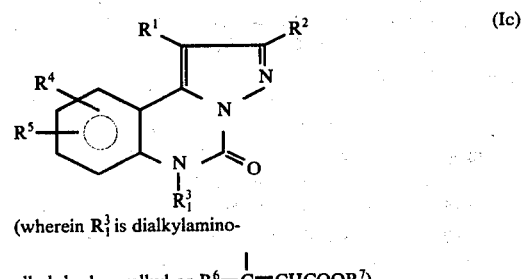

(wherein $R_1^3$ is dialkylamino-alkyl, hydroxyalkyl or $R^6$—$\overset{|}{C}$=CHCOOR$^7$)

Preferred are compounds of formulae Ia, Ib, and Ic wherein $R^4$ and $R^5$ are hydrogen.

The compounds of Formula I of the invention may be prepared by several methods.

One such method involves the preparation of compounds of the structure

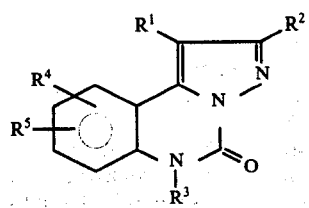

wherein $R^1$ to $R^5$ are as defined hereinbefore. This method (hereinafter called the "first method") involves reacting a substituted acetylene of formula III with a 3-diazoindol-2(3H)one of formula II in accordance with the following reaction scheme:

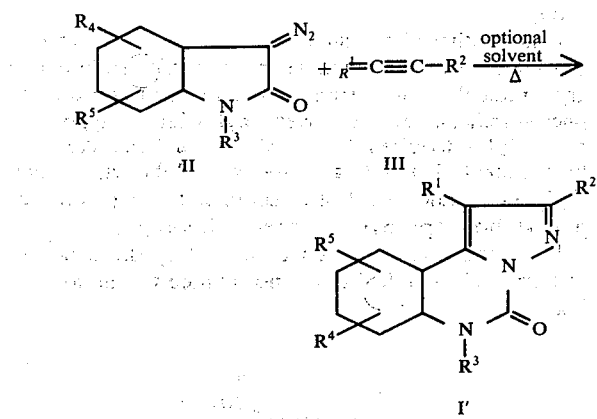

The reaction can be carried out in an excess of the acetylenic compound or in an optional solvent which is essentially inert to both of the reactants. Examples of suitable optional solvents include, among others, aliphatic hydrocarbons, such as pentane, hexane, octane, and the like; aromatic hydrocarbons, such as benzene, toluene, the xylenes, and the like; halogenated hydrocarbons, such as methylene chloride, chloroform, carbon tetrachloride, ethylene dichloride, chlorobenzene, bromobenzene, and the like; ethers, such as diethyl ether, diisopropyl ether, methyl butyl ether, tetrahydrofuran, 1,4-dioxane and the like; aliphatic esters, such as methyl acetate, ethyl acetate, butyl acetate and the like; and miscellaneous solvents, such as N,N-dimethylacetamide, dimethyl sulfoxide, and the like. The aromatic hydrocarbons, such as benzene and toluene and the chlorinated hydrocarbons, such as methylene chloride are preferred. The amount of solvent employed is not critical, but should be sufficient to permit adequate agitation. Typically, the weight-to-volume ratio of reactants to solvent is at least about 1:2 and preferably at least about 1:3, although larger volumes of solvent can be employed if desired. The molar ratio of substituted acetylene to 3-diazoindol-2(3H)-one can vary from about 1:1 to about 100:1. Preferably, the molar ratio will be in the range of from about 1:1 to about 40:1. Reaction time, while to some extent temperature-dependent, can vary from about 15 minutes to about 48 hours. Preferably, the reaction time will be in the range of from about 15 minutes to about 30 hours. The reaction is normally carried out at an elevated temperature, i.e., from about 40° C. to about 150° C., conveniently at the reflux temperature of the solvent, if used, or below about 150° C. A reaction temperature of from about 70° C. to about 120° C. is preferred. Isolation of the compounds of formula I is accomplished by standard procedures. With the preferred optional solvents, the pyrazolo[1,5-c]quinazolin-5(6H)-one is relatively insoluble at ambient temperature or lower, and isolation of the reaction product is accomplished by cooling the reaction mixture and removing the precipitate.

In the absence of solvent, the remaining excess substituted acetylene can be optionally removed by distillation in vacuo; the product is isolated by triturating the distillation residue with a preferred solvent followed by filtration of the precipitated product. If desired, the pyrazolo[1,5-c]quinazolin-5(6H)-one can be recrystallized from additional reaction solvent.

The substituted acetylene preferably reacts with the 3-diazoindol-2(3H)-one to give a pyrazolo[1,5-c]quinazolin-5(6H)-one having $R^1$ in the 1-position. However, reverse addition can occur which results in $R^2$ being in the 1-position. Such reverse addition is now favored, and when $R^1$ is hydrogen or lower alkoxycarbonyl, little if any reverse addition product is formed. The presence of reverse addition compound is not detrimental to the isolation and purification of the desired product. However when $R^1$ is $C_1$-$C_4$ alkyl, phenyl, or monosubstituted phenyl, the amount of reverse addition product which is formed increases with increasing bulk of $R^1$.

The substituted acetylenes employed in the abovedescribed processes in general are commercially available or readily prepared by well-known procedures.

The 3-diazoindol-2(3H)-ones employed in the abovedescribed processes in general are prepared from the corresponding isatin compound. The preparation of isatin compounds is well known in the art. The required N-substituted isatin is obtained by either of two routes, depending upon whether the N-substituent is attached by an (1) alkyl or aralkyl carbon atom or (2) aryl carbon atom. When the desired isatin nitrogen substituent is attached by an alkyl or aralkyl carbon atom, the isatin compound is prepared by N-alkylation of the parent compound with an alkyl or aralkyl halide or by an unsaturated conjugated ester, such as a substituted propiolate ester in the optional presence of a strong base such as, for example, sodium hydride. However, when an aryl substituent on the isatin nitrogen is desired, a different procedure must be employed. In that case, the desired N-aryl isatin is prepared directly by cyclization with oxalyl chloride of an appropriately-substituted diarylamine.

Once the desired isatin has been obtained, the corresponding 3-diazoindol-2(3H)-one is prepared in accordance with known procedures. See, for example, J. M. Michowski, Tetrahedron Letters, 1773 (1967) and M. P. Cava, et al., J. Am. Chem. Soc., 80, 2257 (1958). The appropriate isatin compound is treated with p-toluenesulfonylhydrazine. The resulting hydrazone then is treated with a base such as aqueous sodium hydroxide or aluminum oxide to give the desired 3-diazoindol-2(3H)-one.

Compounds of formula I wherein $R^4$ and/or $R^5$ are OH are prepared by reacting compounds of formula I, wherein $R^4$ and/or $R^5$ are

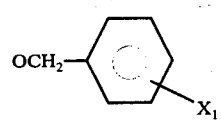

with an appropriate reducing agent under selective conditions in an inert organic solvent.

Typical reducing agents include a metal catalyst, preferably Raney nickel, and hydrogen in the optional presence of a hydrogen halide in an inert organic solvent. Typical solvents include alkanols of 1-6 carbons such as methanol, ethanol and the like. The preferred optional hydrogen halides are hydrogen chloride and hydrogen bromide. The reactions are carried out for from about 1/6 hour to about 92 hours, preferably for from about ½ to about 24 hours to from about −20° to about 100° C.

The last-mentioned compounds of formula I can also be prepared by reacting the last-mentioned starting materials of formula I with at least about 0.5, preferably at least about 0.8, molar equivalents of an inorganic hydrogen halide (preferably hydrogen chloride, hydrogen bromide and hydrogen fluoride) or with a halogenated alkyl carboxylic acid of 1–4 carbons, preferably trifluoroacetic acid. The reaction is run in anhydrous hydrogen fluoride, or, when employing other acids, in an optional inert solvent.

Typical solvents include alkyl carboxylic acids of 1–3 carbons, such as acetic acid and the like; ethers such as diethyl ether, dioxane, tetrahydrofuran and the like; alkanols of 1–6 carbons such as methanol, ethanol, and the like; alkyl esters wherein both the acid and the alcohol from which the ester is derived may have from 1–4 carbon atoms such as ethyl acetate, propyl acetate, ethyl propionate and the like; halogenated hydrocarbons such as methylene chloride, chloroform, di-, tri- and tetrachloroethanes and the like; nitroalkanes of 1–4 carbons such as nitromethane, nitroethane and the like; or alkyl ketones having alkyl radicals of 1–4 carbons such as acetone, methylethyl ketone and the like.

The reaction is carried out at from about $-50°$ to about 200° C., preferably from about 0° to about 120° C., until a significant amount of end product is obtained, typically, for from about 1/10 to about 92, preferably from about 1/6 to about 30 hours. The product is isolated by conventional techniques. For example, with all acids except hydrogen fluoride, the reaction mixture is diluted with an inert water-immiscible organic solvent, washed with dilute aqueous sodium bicarbonate, dried and chromatographed. When using hydrogen fluoride, the hydrogen fluoride is evaporated, the residue dissolved in an inert organic solvent, such as halogenated hydrocarbons, e.g., methylene chloride, chloroform or trichloroethylene; alkyl esters wherein both the acid and the alcohol from which the ester is derived may have from 1–4 carbon atoms, e.g., ethyl acetate, propyl acetate, ethyl propionate and the like, washed with water, dried and chromatographed.

Compounds of formula I wherein $R^4$ and/or $R^5$ are lower alkoxy are also prepared by reacting compounds of formula I wherein $R^4$ and/or $R^5$ are hydroxyl and where $R^3 \neq H$ or, if $R^3 = H$, the product may have $R^3 =$ lower alkyl group of $R^4$ and/or $R^5$, with from about 0.5 to about 12, preferably from about 0.8 to about 3.0 molar equivalents of an appropriate base, e.g., $KHCO_3$, followed by reaction of the thus formed salt with a corresponding molar equivalent of an appropriate alkylating agent of formula lower alkyl-M wherein M is any group which is compatible with lower alkyl (1–4 carbons), and capable of being displaced by aryloxide anion under the reaction conditions. Some typical M groups include halogen, preferably chlorine, bromine, iodine;

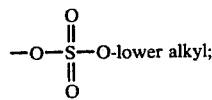

or an alkyl or arylsulfonate of formula

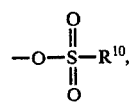

wherein $R^{10}$ can be alkyl of 1–6 carbons or aryl of from about 6 to 10 carbons optionally substituted by halogen, nitro or alkyl of 1–3 carbons. The reaction is run in an essentially inert organic solvent, e.g., lower alkyl ketones, such as methyl ethyl ketone.

Other typical bases include alkali metals (preferably lithium, sodium and potassium) and their salts of alkanols of 1–6 carbons such as methanol, ethanol, i-propanol, t-butyl alcohol, n-amyl alcohol and the like; of ammonia; of mono- and dialkylamines wherein the alkyl groups contain from 1–6 carbons such as ethylamine, diethylamine, di-isopropylamine, cyclohexyl isopropylamine and the like; of acidic hydrocarbons such as triphenylmethane and the like; thallous salts of the preceding alkanols; alkali metal (preferably sodium) hydrides.

Other typical organic solvents include alkanols of 1–5 carbons such as methanol, ethanol, t-butyl alcohol, n-butanol and the like; ethers of 4–12 carbons such as tetrahydrofuran, dioxane, diphenyl ether, 1,2-dimethoxyethane and the like; N,N-dialkylformamides, N,N-dialkylalkanoylamides wherein the alkyl and alkanoyl radicals have 1–4 carbons, such as dimethylformamide, dimethylacetamide and the like; dialkyl sulfoxides of 3–5 carbons such as dimethylsulfoxide and the like; hexamethylphosphorous triamide.

The reaction is carried out at from about $-20°$ C. to about 300° C., preferably from about 0° C. to about 100° C. for from about 0.2 hour to about 96 hours, preferably from about 0.5 hour to about 72 hours.

The products are isolated by conventional techniques. For example, the reaction mixture is refluxed for 5 hours, cooled, adjusted to pH 6 with aqueous HCl and evaporated; the residue is diluted with a water-immiscible, inert solvent such as methylene chloride, washed with water, dried and chromatographed.

In the above reaction when $R^3 = H$ in the starting material, the resultant product may have $R^3 =$ lower alkyl, depending on the strength of the base used and on the relative amount of alkylating agent employed in the reaction.

Compounds of formula I wherein $R^4$ and $R^5$ are other than OH and $R^3$ is other than hydrogen or optionally substituted phenyl are also prepared by reacting compounds of formula I wherein $R^3$ is hydrogen with from about 0.5 to about 2, preferably from about 0.8 to about 1.3 molar equivalents of an appropriate base, followed by reaction of the thus formed salt with a corresponding molar equivalent of an appropriate alkylating agent of formula $R^3$—M wherein $R^3$ is other than hydrogen or optionally substituted phenyl and M is any group which is compatible with $R^3$ and capable of being displaced by the salt under the reaction conditions. Some typical M groups include halogen, preferably chlorine, bromine, iodine;

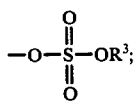

or an alkyl or arylsulfonate of formula

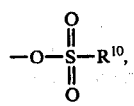

where $R^{10}$ can be alkyl of 1–6 carbons or aryl of from about 6 to 10 carbons optionally substituted by halogen, nitro or alkyl of 1-3 carbons. The reaction is run in an essentially inert organic solvent.

Typical bases include alkali metals (preferably lithium, sodium and potassium) and their salts of alkanols of 1-6 carbons such as methanol, ethanol, i-propanol, t-butyl alcohol, n-amyl alcohol and the like; of ammonia; of mono- and dialkylamines wherein the alkyl groups contain from 1-6 carbons such as ethylamine, diethylamine, di-isopropylamine, cyclohexyl isopropylamine and the like; of acidic hydrocarbons such as triphenylmethane and the like; thallous salts of the preceding alkanols, and, preferably, alkali metal hydrides such as sodium hydride.

Typical organic solvents include alkanols of 1-5 carbons such as methanol, ethanol, t-butyl alcohol, n-butanol and the like; ethers of 4-12 carbons such as tetrahydrofuran, dioxane, diphenyl ether, 1,2-dimethoxyethane and the like; N,N-dialkylformamides, N,N-dialkylalkanoylamides wherein the alkyl and alkanoyl radicals have 1-4 carbons, such as dimethylformamide, dimethylacetamide and the like; dialkyl sulfoxides, hexamethylphosphorous triamide and their mixtures.

The reaction is carried out at from about $-20°$ to about 300° C., preferably from about 0° to about 100° C. for from about 0.2 hour to about 96 hours, preferably from about 0.5 hour to about 72 hours.

The products are isolated by conventional techniques. For example, the reaction mixture is evaporated; the residue is neutralized with aqueous acid, extracted with a water-immiscible, inert solvent such as methylene chloride, washed with water, dried and chromatographed.

More specifically, compounds of the invention of the structure

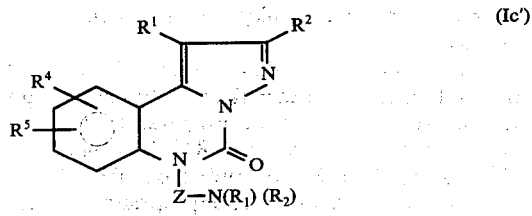

(Ic')

wherein $R_1$ and $R_2$ are the same or different and are hydrogen or lower alkyl and Z is a straight or branched chain alkylene group containing from 1 to about 6 carbons in the normal chain, may be prepared by reaction of a starting pyrazolo[1,5-c]quinazoline of the structure

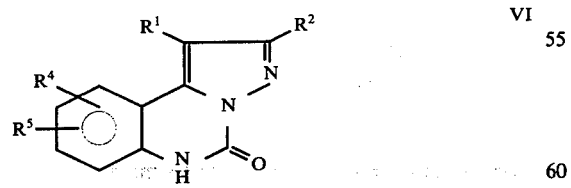

VI with a thallous alkoxide in the presence of an aprotic solvent, such as dimethylformamide and/or diethyl ether, and then reacting same with an aminoalkyl halide of the structure

X—Z—N($R_1$)($R_2$)          VII where X is halogen preferably chlorine, bromine or iodine, in the presence of an aromatic solvent such as toluene, benzene, xylene and the like.

Compounds of the structure

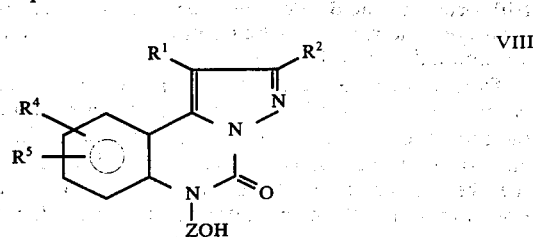

VIII wherein Z is as defined above are prepared by reacting a starting pyrazolo[1,5-c]quinazoline of the structure

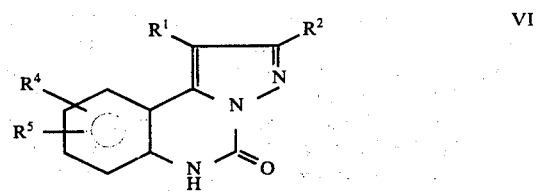

VI with a thallous alkoxide in the presence of an aprotic solvent, such as dimethylformamide and/or diethyl ether, to form the corresponding thallium salt which is reacted with a dihaloalkane of the structure

X—Z—X'          IX wherein X and X' are the same or different and are each halogen, in refluxing toluene or other aromatic solvent to form the corresponding haloalkylene derivative. The haloalkylene derivative is then acyloxylated by reaction with, for example, potassium acetate, in the presence of acetone and potassium iodide to give the corresponding acyloxyalkylene derivative which is then reacted with a mineral acid, such as hydrochloric acid, in an alcohol, such as methanol, to form the compound of structure VIII.

Compounds of the structure

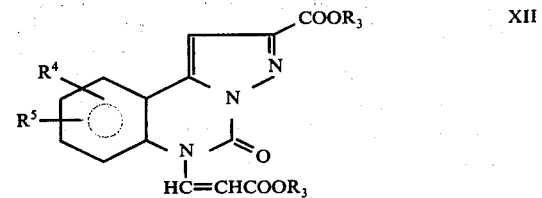

XII may be prepared by reacting a compound of the structure

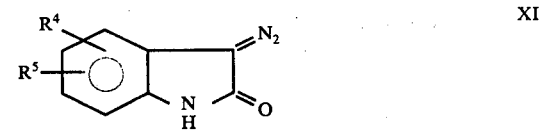

XI with an excess of a compound of the structure

HC≡CCOOR$_3$          XII in the presence of an appropriate solvent such as benzene, in a nitrogen atmosphere while heating the reaction mixture at reflux for 5 to 48 hours.

Compounds of the structure

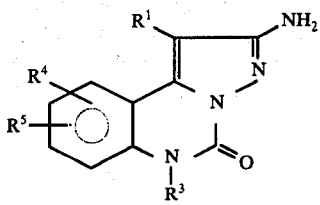

may be prepared by selectively hydrolyzing compounds of structure

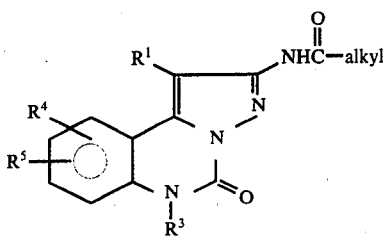

with an appropriate base, such as potassium hydroxide, in an organic solvent, such as ethanol, in the optional presence of water under selective conditions, such as at reflux for 3 hours, choosen to avoid, or minimize, cleavage of the pyrimidone ring.

Compounds of structure XIV may be prepared by reacting compounds of the structure

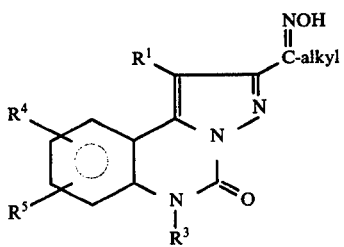

with an appropriate "Beckmann rearrangement" reagent, such as polyphosphoric acid, or other similar well-known reagents at a temperature of approximately 135° for about 10 minutes.

Compounds of structure XV may be prepared by the reaction of compounds of structure

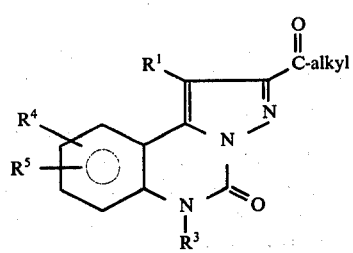

with hydroxylamine in the optional presence of an acid, such as hydrogen chloride, in an organic solvent, such as pyridine at ambient temperatures, or higher, for about 18 hours.

The starting materials of structure XVI are known or available by methods well known to those skilled in the art.

Starting materials or final products that are mixtures of isomers can be separated into the single isomers by methods in themselves known, e.g., by fractional distillation, crystallization and/or chromatography. Racemic products can likewise be resolved into the optical antipodes, for example by separation of diastereomeric salts thereof, e.g., of the fractional crystallization, in the case of basic compounds, of d- or l-tartrates, maleates, -mandelates, —N-acetylphenylalaninates or -camphor sulfonates, or, in the case of acid compounds, d- or l-α-methylbenzylamine and reconverting the diastereomeric salts into the free antipodes.

Certain of the compounds of formula I may form physiologically acceptable acid-addition salts or base addition salts with inorganic and organic acids or alkali metal or alkaline earth metal bases such as sodium hydroxide or calcium hydroxide. These salts frequently provide useful means for isolating the products from reaction mixtures by forming the salt in a medium in which it is insoluble. The free base may then be obtained by neutralization, e.g., with a base or acid. Then any other salt may again be formed from the free base and the appropriate inorganic acid or base. Illustrative are the hydrohalides, especially the hydrochloride and hydrobromide which are preferred, sulfate, nitrate, phosphate, oxalate, tartrate, maleate, fumarate, citrate, succinate, methanesulfonate, benzenesulfonate, toluenesulfonate, and the like.

The compounds of formula I, and their pharmaceutically acceptable salts, are useful in treating various allergic conditions in mammalian species such as mice, cats, dogs, etc., when administered in amounts ranging from about 1 milligram to about 500 milligrams per kilogram of body weight per day. The compounds can be used prophylactically or therapeutically to treat various allergic and immunological disorders and in particular to treat certain types of asthma, hay-fever, and rhinitis. A preferred dosage regimen would be from about 3 milligrams to about 200 milligrams per kilogram of body weight per day administered in a single dose or plurality of divided doses.

The compounds of formula I, and the pharmaceutically acceptable salts thereof, are anti-allergics which inhibit the effects of certain antigen-antibody reactions and in particular inhibit the release of mediators such as histamine. The anti-allergy activity of these compounds is determined by the reaginic antibody induced passive cutaneous anaphylaxis (PCA) reaction in rats. (See Bach, Immediate Hypersensitivity: Laboratory Models and Experimental Findings, Ann. Rep. Med. Chem., 7: 238–248 (1972), for a discussion of the predictability of clinical efficacy of compounds active in the PCA).

A compound of formula I, or a salt thereof, can be administered by the inhalation of an aerosol or powder as described in U.S. Pat. No. 3,772,336 (i.e., breathing finely divided particles of the active ingredient into the lungs), orally, or parenterally. Powders can be prepared by comminuting the active ingredient with a similarly comminuted diluent such as starch or lactose. Suitable forms for oral administration include capsules, tablets, and syrups, and a suitable form for parenteral administration is a sterile injectable. Such unit dosage forms are prepared by compounding with a conventional vehicle, excipients, binders, preservatives, stabilizers, flavoring agents or the like as called for by acceptable pharmaceutical practice. Also, the compounds of this invention can be formulated with other pharmaceutically active compounds such as bronchodilators, steroids, antihistamines, etc.

The compounds of the invention are also useful as antiinflammatory agents as determined by the reverse passive arthus test [Agents & Actions, 5, 39 (1975)] and are effective in the prevention and inhibition of granuloma formation in warm blooded animals, and may be used, for example, in a manner similar to phenylbutazone or indomethacin. They may be used to decrease joint swelling, tenderness, pain and stiffness is mammalian species, such as dogs and monkeys, e.g., in conditions such as rheumatoid arthritis.

Furthermore, the compounds of the invention are useful in mammals as inhibitors of 3',5'-cyclic adenosine phosphodiesterase and 3',5'-cyclic guanosine phosphodiesterase, as well as anxiolytic agents at a dosage level of from about 12 to about 100 mg/kg per day ip in one dose or in up to 4 divided doses; as inhibitors of platelet aggregation in vitro and therefore of potential use in the treatment of thrombosis.

The compounds of the present invention in the described dosages may be administered orally; however, other routes such as intraperitoneally, subcutaneously, intramuscularly or intravenously may be employed.

The active compounds of the present invention are orally administered, for example, with an inert diluent or with an assimilable edible carrier, or they may be enclosed in hard or soft gelatin capsules, or they may be compressed into tablets, or they may be incorporated directly with the food of the diet. For oral therapeutic administration, the active compounds of this invention may be incorporated with excipients and used in the form of tablets, troches, capsules, elixirs, suspensions, syrups, wafers, chewing gum, and the like. The amount of active compound in such therapeutically useful compositions or preparations is such that a suitable dosage will be obtained.

The tablets, troches, pills, capsules and the like may also contain the following: a binder such as gum tragacanth, acacia, corn starch or gelatin; an excipient such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain in addition to materials of the above type a liquid carrier such as a fatty oil. Various other materials may be present as coatings or to otherwise modify the physical form of the dosage unit, for instance, tablets, pills or capsules may be coated with shellac, sugar, or both. A syrup or elixir may contain the active compounds, sucrose as a sweetening agent, methyl and propyl parabens as preservations, a dye and a flavoring such as cherry or orange flavor. Of course, any material used in preparing any dosage unit form should be pharmaceutically pure and substantially non-toxic in the amounts employed.

The following Examples further illustrate and represent preferred embodiments of the invention. All temperatures are expressed in degrees Centigrade.

EXAMPLE 1

6-[2-(Dimethylamino)ethyl]pyrazolo[1,5-c]quinazolin-5(6H)-one 11.1 g (0.060 mole) of pyrazolo[1,5-c]quinazolin-5(6H)-one is dissolved in 500 ml of dimethylformamide and treated with 15.0 g (0.060 mole) of thallous ethoxide. The resultant suspension is stirred for 1.5 hours and then 1 liter of diethyl ether added. The yellow solid is filtered, washed with ether, and dried to give 22 g of thallium salt.

This is suspended in 800 ml of refluxing toluene. A solution of dimethylaminoethyl bromide in toluene is prepared by treating 21 g (0.090 mole) of the hydrobromide salt with 100 ml of 1 M potassium carbonate solution, extracting the free base into toluene and drying with sodium sulfate. The free base in toluene is added to the thallium salt suspension and refluxed for 3 hours. After this, another solution of free base, prepared precisely as before, is added and the mixture refluxed for an additional 15 hours.

The hot reaction mixture is filtered and the filtrate stripped to a yellow oil residue (13 g). The oil is dissolved in chloroform and chromatographed on a 250 g-dry silica gel (Baker) column. Elution with 1 liter of chloroform/methanol (7:3) gives 6.35 g (0.0248 mole) of slightly impure (TLC) product as an oil.

EXAMPLE 2

6-[2-(Dimethylamino)ethyl]pyrazolo[1,5-c]quinazolin-5(6H)-one, maleate salt (1:1)

The oil from Example 1 is dissolved in 50 ml of warm acetonitrile and 1.44 g (0.0124 mole) of solid maleic acid added. After standing for 0.5 hour at room temperature, crystallization occurs and after filtering there results 5.5 g, m.p. 180°–182°. This is twice recrystallized from acetonitrile/ether to give 3.5 g of analytically pure maleate salt.

Anal. Calcd for $C_{18}H_{20}N_4O_5$: C, 58.07; H, 5.42; N, 15.05 Found: C, 58.24; H, 5.72, N, 15.27.

EXAMPLE 3

6-[3-(Dimethylamino)propyl]pyrazolo[1,5-c]quinazolin-5(6H)-one 5.5 g (0.030 mole) of pyrazolo[1,5-c]quinazolin-5(6H)-one is dissolved in 200 ml of dimethylformamide and treated with 7.5 g (0.030 mole) of thallous ethoxide. The suspension that forms is stirred for 2 hours, and then 600 ml of ethyl ether is added. The yellow solid is filtered, washed with ether and dried in vacuo at 25°, weight 11.5 g.

The thallium salt is suspended in 200 ml of refluxing toluene and a toluene solution of 3-dimethylaminopropyl chloride (prepared by treating an aqueous solution of 7.1 g [0.045 mole] of the hydrochloride with 50 ml of 1 M potassium carbonate, extracting the free base into toluene and drying with sodium sulfate) added thereto. The mixture is refluxed for 3 hours, after which another solution of the amine, prepared precisely as above, is added, and the reflux continued for a total of 23 hours.

The reaction mixture is filtered and the toluene removed in vacuo to give 8.0 g of an oil. The oil is dissolved in chloroform and chromatographed on a 240 g-dry silica gel (Baker) column. Elution with 2 l. of chloroform/methanol (9:1) and removal of solvents gives 5.3 g of the title compound.

EXAMPLE 4

6-[3-(Dimethylamino)propyl]pyrazolo[1,5-c]quinazolin-5(6H)-one, maleate salt (1:1)

The oil of Example 3 is dissolved in 50 ml of warm acetonitrile and 2.58 g (0.0222 mole) of solid maleic acid added. A complete solution results from which crystals separate on cooling to room temperature. From this and the mother liquor there is obtained 5.8 g of crystals, which after two recrystallizations from methanol/ether, gives 5.0 g of analytically pure title compound, m.p. 170°–171°.

Anal. Calcd for $C_{19}H_{22}N_4O_5$: C, 59.10; H, 5.76; N, 14.50: Found: C, 59.39; H, 5.86; N, 14.72.

EXAMPLE 5

6-(3-Hydroxypropyl)pyrazolo[1,5-c]quinazolin-5(6H)-one

A. N-Chloropropyl derivative of pyrazolo[1,5-c]quinazolin-5(6H)-one 11.1 g (0.060 mole) of pyrazolo[1,5-c]quinazolin-5(6H)-one is dissolved in 300 ml of dimethylformamide at room temperature and 15.0 g (0.060 mole) of thallium ethoxide added thereto. The suspension which forms is stirred for 1 hour, filtered, washed with ether and dried to give 22 g of the thallium salt.

The salt is suspended in 1 liter of refluxing toluene and 14 g (0.090 mole) of 1-bromo-3-chloropropane added. After 3 hours, another 14 g of alkylating agent is added and the refluxing continued for an additional 9 hours.

The hot reaction mixture is filtered and the filter cake washed several times with boiling chloroform. The combined filtrates are stripped to a yellow solid (9 g). The solid is chromatographed on a 200 g-dry silica gel column, and eluted with 1 liter of chloroform-ethyl acetate (2:3). Recrystallization from acetone gives 5.5 g of the chloropropyl product, m.p. 138°–139°.

B. Acetoxylation of N-chloropropyl derivative of pyrazolo[1,5-c]quinazolin-5(6H)-one 2.7 g (0.0117 mole) of the chloropropyl compound of part A is dissolved in 250 ml of acetone and 1.95 g (0.0117 mole) of potassium iodide and 3.1 g (0.0313 mole) of fused potassium acetate are added.

The reaction mixture is refluxed under nitrogen for 72 hours, after which it is filtered and the filtrate stripped to an oil (3.4 g, quantitative yield). The oil solidifies on standing and is used as such for the subsequent reaction.

C. 6-(3-Hydroxypropyl)pyrazolo[1,5-c]quinazolin-5(6H)-one

The 3.4 g (0.0117 mole) of the acetoxy compound of part B is suspended in 200 ml of methanol and 13 ml of 2.8 N hydrochloric acid in methanol added thereto. The mixture is refluxed under nitrogen for 2 hours and then stripped to a solid residue of 3.0 g. This is chromatographed on a 60 g-dry silica gel column. The column is eluted with 1 liter of chloroform-methanol (9:1) to give 2.0 g of a yellow solid (slightly impure by TLC).

The solid is dissolved in a small amount of chloroform-methanol (1:1) and further purified by preparative chromatography on Merck silica gel plates (20 cm × 20 cm, 2 mm thickness). The plates are developed three times by utilizing a mixture of chloroform-methanol (19:1), and eluting the title compound from the silica gel with chloroform:methanol (1:1). There is obtained 1.5 g of a white solid, m.p. 112°–115°. Recrystallization from dichloromethane-pentane gives 1.4 g of the analytical sample, m.p. 120°–122°.

Anal. Calcd for $C_{13}H_{13}N_3O_2$: C, 64.20; H, 5.39; N, 17.27: Found: C, 64.01; H, 5.51, N, 17.57.

EXAMPLE 6 cis-8-Chloro-6-(3-ethoxy-3-oxo-1-propenyl)-5,6-dihydro-5-oxopyrazolo[1,5-c]quinazoline-2-carboxylic acid, ethyl ester A. Preparation and separation of 4-chloro and 6-chloroisatin Reference: J.A.C.S., 68, 2695 (1946).

To a solution of 245 g (1.48 mole) of chloral hydrate and 1.55 kg of anhydrous sodium sulfate in 4 liters of water is added a solution of 171 g (1.34 mole) of 3-chloroaniline in 800 ml of water and 117.5 ml of concentrated hydrochloric acid followed by a solution of 295 g (4.25 mole) of hydroxylamine hydrochloride in 500 ml of water. The resulting suspension is heated to 100°, cooled to room temperature and extracted with 2 liters of ether. The ether extract is stripped and the solid reextracted with 2 liters of ether. The ether extract is stripped and the solid residue air dried to give 193.4 g (73% yield) of isonitroso-3-chloroacetanilide. This is finely pulverized and added in small portions with stirring over a twenty minute interval to 980 ml of concentrated sulfuric acid held at 80°–85°. The reaction mixture is then heated for 15 minutes at 90°–95°, cooled to room temperature, and poured over cracked ice. The red precipitate is filtered, washed with water and suspended in 2 liters of water and brought into solution by the addition of 390 ml of 3N sodium hydroxide solution. The solution is filtered through Celite and the filtrate carefully adjusted to pH 8.0 with concentrated hydrochloric acid at which point a solution of 39 ml of concentrated hydrochloric acid in 195 ml of water is added. The suspension is stirred for five minutes and filtered, weight 90 g of crude 4-chloroisatin (37% yield based on 3-chloroaniline).

The filtrate is further acidified with 200 ml of concentrated hydrochloric acid, stirred for five minutes and filtered to give 50 g of crude 6-chloroisatin (22% yield based on 3-chloroaniline).

Recrystallization of 90 g of the 4-chloroisatin from absolute ethanol gives 80 g of material, m.p. 256°–258° (lit. 256.5°–258°).

Recrystallization of the 50 g of crude 6-chloroisatin from absolute ethanol gives 43 g of material, m.p. 260°–262° (lit. 258°–259°).

B. Preparation of 6-chloroisatin-3-p-toluenesulfonylhydrazone 32.4 g (0.18 mole) of 6-chloroisatin is dissolved in 6 liters of boiling methanol and 37.2 g (0.198 mole) of p-toluenesulfonylhydrazide added. The solution is concentrated to crystals (steam bath), cooled to 5° and filtered to give 47.3 g (75% yield) of the p-toluenesulfonylhydrazone, m.p. 206°–208° (d).

C. Preparation of 6-chloro-3-diazooxindole 33.8 g of 6-chloroisatin-3-p-toluenesulfonylhydrazone is suspended in a mixture of 970 ml of 0.2 N sodium hydroxide solution and 1.5 liters of dichloromethane. The suspension is heated at 41° for 3 hours with vigorous stirring under nitrogen, cooled to room temperature, filtered and recrystallized from methanol. Yield 13 g (68%), m.p. 197°–199° (d).

D. cis-8-Chloro-6-(3-ethoxy-3-oxo-1-propenyl)-5,6-dihydro-5-oxopyrazolo[1,5-c]quinazoline-2-carboxylic acid, ethyl ester 7.5 g (0.039 mole) of 6-chloro-3-diazooxindole is suspended in 400 ml of xylene and 8.4 g (0.086 mole) of ethyl propiolate added. The reaction mixture is heated 7 hours in a 160° silicone oil bath under nitrogen. A brown solid forms on cooling to room temperature (9.0 g, 59% yield). Recrystallization from dichloromethanemethanol gives 8.5 g of analytically pure title compound, m.p. 215°–217°.

Anal. Calcd for $C_{18}H_{16}N_3O_5Cl$: C, 55.46; H, 4.13; N, 10.78; Cl, 9.10: Found: C, 55.66; H, 4.35; N, 10.82; Cl, 9.25.

EXAMPLE 7–8

2-Aminopyrazolo[1,5-c]quinazolin-5(6H)-one 10.0 g of N-(5,6-dihydro-5-oxopyrazolo[1,5-c]quinazolin-2-yl)acetamide is suspended in 973 ml of 10% ethanolic potassium hydroxide and refluxed for 3 hours. The reaction mixture is concentrated, cooled to room temperature, diluted with water and neutralized with acetic acid. The product is filtered off and dried.

EXAMPLE 9

6-(3-Ethoxy-3-oxo-1-propenyl)-9-methoxy-5,6-dihydro-5-oxopyrazolo[1,5-c]quinazoline-2-carboxylic acid, ethyl ester 1.5 g (0.0079 mole) of 5-methoxy-3-diazooxindole and 0.99 g (0.01 mole of 1.3 equiv.) of 99% ethyl propiolate are refluxed in benzene (50 ml) under $N_2$ for 24 hours. The reaction mixture is cooled down to room temperature and the precipitates that form are filtered off and washed well with ether, dried in a vacuum oven at 60° for 2 hours. Yield: 661.8 mg, m.p. 202°–204°, Rf 0.3. This crude product is taken up in 75 ml of absolute ethanol, treated with activated carbon, filtered through a celite pad and the clear filtrate is concentrated down to a volume of ~50 ml on the steam bath. After cooling, the precipitates that form are filtered off. The product is dried overnight in a vacuum oven at room temperature. Yield: 555.4 mg, m.p. 225°–227°.

The filtrate from the 661.8 mg of crude product is stripped to dryness and the solid obtained triturated with a few ml of methanol followed by ether. The product (Rf 0.66) is air-dried. Yield: 1.15 mg, m.p. 157°–159°. This product is taken up in absolute ethanol (150 ml), concentrated down to a volume of ~50 ml and filtered while hot. The clear filtrate is cooled and the precipitates that form are filtered off and dried overnight in a vacuum oven at room temperature. Yield: 1.01 g, m.p. 153°–154°.

EXAMPLES 10 to 30

Following the procedure of Example 1, but substituting the compounds indicated in Column I, Table I below for pyrazolo[1,5-c]quinazolin-5(6H)-one and the aminoalkylhalide indicated in Column II below for dimethylaminoethyl bromide in Example I, the compounds indicated in Column III are obtained.

TABLE I

| | Column I | | | Column II | | | Column III | | | | |
|---|---|---|---|---|---|---|---|---|---|---|---|
| Ex. No. | $R^4$ (position) | $R^5$ (position) | X | Z | $R_1$ | $R_2$ | $R^4$ (position) | $R^5$ (position) | $R_1$ | $R_2$ | Z |
| 10. | H | H | Br | $-CH_2-$ | $CH_3$ | H | as in Column I | | as in Column II | | |
| 11. | H | H | Cl | $-(CH_2)_2-$ | H | H | | | | | |
| 12. | H | H | Br | $-(CH_2)_3-$ | $C_2H_5$ | $C_2H_5$ | | | | | |
| 13. | $CH_3(10)$ | H | Cl | $-CH_2-$ | $n-C_3H_7$ | $CH_3$ | | | | | |
| 14. | H | H | Br | $\begin{array}{c}CH_3\\\|\\-CH-\end{array}$ | $CH_3$ | $CH_3$ | | | | | |
| 15. | $CH_3O(10)$ | H | Cl | $-CH_2-$ | $C_2H_5$ | H | | | | | |
| 16. | $CH_3O(9)$ | H | Cl | $\begin{array}{c}CH_3\\\|\\-CH-\\\|\\CH_2-CH_3\end{array}$ | $s-C_4H_9$ | $CH_3$ | | | | | |
| 17. | $CH_3O(8)$ | H | Br | $-CH_2-$ | $-CH_2-\bigcirc$ | H | | | | | |
| 18. | $C_2H_5O(9)$ | H | Br | $\begin{array}{c}CH_3\\\|\\-CH_2-CH\end{array}$ | H | H | | | | | |
| 19. | H | H | Cl | $\begin{array}{c}CH_3\\\|\\-CH_2-C-CH_2-\\\|\\CH_3\end{array}$ | $CH_3$ | $CH_3$ | | | | | |
| 20. | $CH_3O(5)$ | H | Br | $-CH_2-$ | $CH_3$ | H | | | | | |
| 21. | $CH_3O(7)$ | H | Br | $-CH_2-$ | $n-C_4H_9$ | H | | | | | |
| 22. | H | H | Br | $-CH_2-$ | $CH_3$ | $CH_3$ | | | | | |
| 23. | F(9) | H | Cl | $\begin{array}{c}C_2H_5\\\|\\-CH-\end{array}$ | $C_2H_5$ | $C_2H_5$ | | | | | |
| 24. | $CH_3(9)$ | H | Cl | $\begin{array}{c}CH_3\\\|\\-CH_2-CH\end{array}$ | $i-C_4H_9$ | $CH_3$ | | | | | |

TABLE I-continued

| | Column I | | Column II | | | Column III | | | |
|---|---|---|---|---|---|---|---|---|---|
| | (structure with $R^4$, $R^5$, pyrazole, NH-C=O) | | X—Z—N($R_1$)($R_2$) | | | (structure with $R^4$, $R^5$, pyrazole, N-Z-N($R_1$)($R_2$)) | | | |
| Ex. No. | $R^4$ (position) | $R^5$ (position) | X | Z | $R_1$ | $R_2$ | $R^4$ (position) | $R^5$ (position) | $R_1$ $R_2$ Z |
| 25. | $CH_3$(8) | $CH_3$(9) | Br | —$(CH_2)_2$— | H | H | as in Column I | as in Column II | |
| 26. | $CF_3$(7) | H | Br | —$CH_2$— | $CH_3$ | $CH_3$ | | | |
| 27. | $NO_2$(9) | H | Br | —$CH_2$— | i-$C_3H_7$ | $CH_3$ | | | |
| 28. | H | H | Br | —$(CH_2)_3$— | s-$C_4H_9$ | H | | | |
| 29. | Cl(10) | H | Br | $CH_3$<br>\|<br>—CH—$CH_2$— | $CH_3$ | $CH_3$ | | | |
| 30. | H | H | Cl | —CH—<br>\|<br>(cyclohexyl) | $CH_3$ | $C_2H_5$ | | | |

EXAMPLES 31 to 51

Following the procedure of Example 5, but substituting the compounds indicated in Column I, Table II below for pyrazolo[1,5-c]quinazolin-5(6H)-one, the dihaloalkane indicated in Column II below for 1-bromo-3-chloropropane in 5A, and the metal acylate indicated in Column III below for potassium acetate in 5B, the compounds indicated in Column IV are obtained.

TABLE II

| | Column I | | Column II | | | Column III | Column IV | | | |
|---|---|---|---|---|---|---|---|---|---|---|
| | (structure) | | X—Z—$X^1$ | | | $MOCR_3$ (with C=O) | (structure with ZOCR₃) | | | |
| Ex. No. | $R^4$ (position) | $R^5$ (position) | X | $X^1$ | Z | $R_3$ | M | $R^4$ (position) | $R^5$ (position) | Z $R_3$ |
| 31. | H | H | Cl | Br | —$CH_2$— | $CH_3$ | K | as in Column I | as in Column II | as in Column III |
| 32. | H | H | Cl | Br | —$(CH_2)_2$— | H | K | | | |
| 33. | H | H | Cl | Cl | —$(CH_2)_3$— | $C_2H_5$ | K | | | |
| 34. | $CH_3$(10) | H | Cl | Br | —$CH_2$— | n-$C_3H_7$ | Na | | | |
| 35. | H | H | Br | Br | $CH_3$<br>\|<br>—CH— | —$CH_3$ | K | | | |
| 36. | $CH_3O$(10) | H | Cl | Cl | —$CH_2$— | $C_2H_5$ | K | | | |
| 37. | $CH_3O$(10) | H | Cl | Br | $CH_3$<br>\|<br>—CH—<br>\|<br>$CH_2$—$CH_3$ | s-$C_4H_9$ | Na | | | |
| 38. | $CH_3O$(10) | H | Cl | Br | —$CH_2$— | —$CH_2$—(phenyl) | Na | | | |
| 39. | $C_2H_5O$(9) | H | Cl | Cl | $CH_3$<br>\|<br>—$CH_2$—CH— | (phenyl) | Na | | | |
| 40. | H | H | Cl | Br | $CH_3$<br>\|<br>—$CH_2$—C—$CH_2$—<br>\|<br>$CH_3$ | —$CH_2$—(methylphenyl) | K | | | |
| 41. | $CH_3O$(5) | H | Br | Cl | —$CH_2$— | —$CH_2$—(chlorophenyl) | K | | | |
| 42. | $CH_3O$(7) | H | Cl | Br | —$CH_2$— | n-$C_4H_9$ | K | | | |
| 43. | H | H | Br | Br | —$(CH_2)_2$— | $CH_3$ | Na | | | |
| 44. | F(9) | H | Br | Br | $C_2H_5$<br>\|<br>—CH— | $C_2H_5$ | Na | | | |
| 45. | $CH_3$(9) | H | Cl | Cl | $CH_3$<br>\|<br>—$CH_2$—CH— | i-$C_4H_9$ | K | | | |
| 46. | $CH_3$(8) | $CH_3$(9) | Cl | Cl | —$CH_2$— | H | K | | | |
| 47. | $CF_3$(7) | H | Br | Br | —$(CH_2)_2$— | $CH_3$ | K | | | |
| 48. | $NO_2$(9) | H | Br | Cl | —$CH_2$— | i-$C_3H_7$ | Na | | | |
| 49. | H | H | Cl | Cl | —$(CH_2)_3$— | s-$C_4H_9$ | K | | | |

TABLE II-continued

| | Column I | Column II | Column III | Column IV | | | | |
|---|---|---|---|---|---|---|---|---|
| | 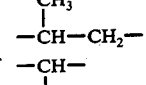 | $X-Z-X^1$ | $MOCR_3$ (O double bond) |  | | | | |
| Ex. No. | $R^4$ (position) | $R^5$ (position) | X  X¹  Z | $R_3$ | M | $R^4$ (position) | $R^5$ (position) | Z | $R_3$ |
| 50. | Cl(10) | H | Cl  Br  $-\overset{CH_3}{\underset{}{CH}}-CH_2-$ | $CH_3$ | K | as in Column I | | as in Column II | as in Column III |
| 51. | H | H | Br  Br  $-\underset{\underset{C_6H_{11}}{\mid}}{CH}-$ | $CH_3$ | Na | | | | |

EXAMPLES 52 to 72

Following the procedure of Example 5C, but substituting the compounds indicated in Column I, Table III below for 6-(3-acetyloxypropyl)pyrazolo[1,5-c]quinazolin-5(6H)-one prepared in Examples 31 to 51, respectively, the compounds indicated in Column II are obtained.

TABLE III

| | | | Column I | | | | Column II | | |
|---|---|---|---|---|---|---|---|---|---|
| | | | 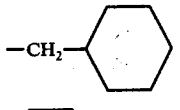 | | | | 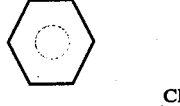 | | |
| Ex. No. | $R^4$ (position) | $R^5$ (position) | Z | $R_3$ | | $R^4$ (position) | $R^5$ (position) | Z | $R_3$ |
| 52. | H | H | $-CH_2-$ | $CH_3$ | | as in Column I | | | |
| 53. | H | H | $-(CH_2)_2-$ | H | | | | | |
| 54. | H | H | $-(CH_2)_3-$ | $C_2H_5$ | | | | | |
| 55. | $CH_3(10)$ | H | $-CH_2-$ | $n-C_3H_7$ | | | | | |
| 56. | H | H | $-\overset{CH_3}{\underset{}{CH}}-$ | $CH_3$ | | | | | |
| 57. | $CH_3O(10)$ | H | $-CH_2-$ | $C_2H_5$ | | | | | |
| 58. | $CH_3O(10)$ | H | $-\overset{CH_3}{\underset{CH_2-CH_3}{CH}}-$ | $s-C_4H_9$ | | | | | |
| 59. | $CH_3O(10)$ | H | $-CH_2-$ | $-CH_2-C_6H_{11}$ | | | | | |
| 60. | $C_2H_5O(9)$ | H | $-CH_2-\overset{CH_3}{\underset{}{CH}}-$ | $-C_6H_5$ | | | | | |
| 61. | H | H | $-CH_2-\overset{CH_3}{\underset{CH_3}{C}}-CH_2-$ | 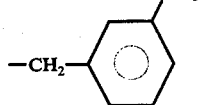 | | | | | |
| 62. | $CH_3O(5)$ | H | $-CH_2-$ | 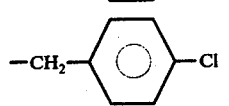 | | | | | |
| 63. | $CH_3O(7)$ | H | $-CH_2-$ | $n-C_4H_9$ | | | | | |
| 64. | H | H | $-(CH_2)_2-$ | $CH_3$ | | | | | |
| 65. | F(9) | H | $-\overset{C_2H_5}{\underset{}{CH}}-$ | $C_2H_5$ | | | | | |
| 66. | $CH_3(9)$ | H | $-CH_2-\overset{CH_3}{\underset{}{CH}}-$ | $i-C_4H_9$ | | | | | |

TABLE III-continued

Column I: structure with $R^4$, $R^5$ on bicyclic with pyrazole, N-acyl, ZOCR$_3$ group Column II: structure with $R^4$, $R^5$ on bicyclic with pyrazole, N-acyl, ZOH group

| Ex. No. | $R^4$ (position) | $R^5$ (position) | Z | $R_3$ | $R^4$ (position) | $R^5$ (position) | Z | $R_3$ |
|---|---|---|---|---|---|---|---|---|
| 67. | CH$_3$(8) | CH$_3$(9) | —CH$_2$— | H | | | | |
| 68. | CF$_3$(7) | H | —(CH$_2$)$_2$— | CH$_3$ | | as in Column I | | |
| 69. | NO$_2$(9) | H | —CH$_2$— | i-C$_3$H$_7$ | | | | |
| 70. | H | H | —(CH$_2$)$_3$— | s-C$_4$H$_9$ | | | | |
| 71. | H | H | $\begin{array}{c}\text{CH}_3\\ \mid\\ \text{—CH—CH}_2\text{—}\end{array}$ | CH$_3$ | | | | |
| 72. | H | H | —CH— (with phenyl substituent) | CH$_3$ | | | | |

EXAMPLES 73 to 90

Following the procedure of Example 6, but substituting the compounds indicated in Column I, Table IV below for 3-diazooxindole, and the compounds indicated in Column II below for ethyl propiolate, the compounds indicated in Column III are obtained.

TABLE IV

Column I: 3-diazooxindole structure with $R^4$, $R^5$

Column II: H—C≡Z—COOR$_3$

Column III: product structure with Z;ab,4 CO$_2$R$_3$, HC=ZH—CO$_2$R$_3$

| Ex. No. | $R^4$ (position) | $R^5$ (position) | Z | $R_3$ | $R^4$ (position) | $R^5$ (position) | Z | $R_3$ |
|---|---|---|---|---|---|---|---|---|
| 73. | H | H | — | CH$_3$ | H | as per Column I | | as per Column II |
| 74. | H | H | — | n-C$_3$H$_7$ | H | | | |
| 75. | H | H | — | phenyl-OC$_2$H$_5$ | | | | |
| 76. | CH$_3$O(4) | H | — | phenyl | CH$_3$O(10) | | | |
| 77. | CH$_3$O(4) | H | — | s-C$_4$H$_9$ | CH$_3$O(10) | | | |
| 78. | CH$_3$O(5) | H | — | phenyl-CF$_3$ | CH$_3$O(9) | | | |
| 79. | CH$_3$O(4) | H | —CH$_2$— | phenyl | CH$_3$O(10) | | | |
| 80. | CH$_3$O(6) | H | — | phenyl-CH$_3$ | CH$_3$O(8) | | | |
| 81. | H | H | —CH$_2$— | phenyl | H | | | |
| 82. | H | H | — | n-C$_3$H$_7$ | H | | | |

TABLE IV-continued

| | Column I | | | | Column III | | | |
|---|---|---|---|---|---|---|---|---|
| | | | | Column II | | | | |
| | | | | H—C≡Z—COOR$_3$ | | | | |
| Ex. No. | R$^4$ (position) | R$^5$ (position) | Z | R$_3$ | R$^4$ (position) | R$^5$ (position) | Z | R$_3$ |
| 83. | H | H | —CH$_2$— | —C$_6$H$_4$—OC$_2$H$_5$ | H | as per Column I | as per Column II | |
| 84. | CH$_3$O(4) | H | —(CH$_2$)$_2$— | —C$_6$H$_5$ | CH$_3$O(10) | | | |
| 85. | CH$_3$O(4) | H | —CH(CH$_3$)— | s-C$_4$H$_9$ | CH$_3$O(10) | | | |
| 86. | CH$_3$O(5) | H | — | —C$_6$H$_4$—CF$_3$ | CH$_3$O(9) | | | |
| 87. | CH$_3$O(4) | H | —CH$_2$— | —C$_6$H$_5$ | CH$_3$O(10) | | | |
| 88. | CH$_3$O(6) | H | —CH$_2$— | —C$_6$H$_4$—CH$_3$ | CH$_3$O(8) | | | |
| 89. | F(5) | H | — | n-C$_4$H$_9$ | F(9) | | | |
| 90. | CH$_3$(5) | CH$_3$(6) | — | —C$_6$H$_5$ | CH$_3$(9) | CH$_3$(8) | | |

EXAMPLE 91

2-[1-(Hydroxyimino)ethyl]pyrazolo[1,5-c]quinazolin-5(6H)-one 1.5 g (0.0066 mole) of 1-acetylpyrazolo[1,5-c]quinazolin-5(6H)-one and 2.8 g of hydroxylamine hydrochloride in pyridine are stirred overnight at room temperature. The reaction mixture is poured into 450 ml ice-water and stirred for 30 minutes. The fine white precipitates that form are filtered off, washed well with water and dried in vacuo at ~90° for 20 hours. Yield: 1.4 g, m.p. 340°–342°; 87.5%.

EXAMPLE 92

N-(5,6-Dihydro-5-oxopyrazolo[1,5-c]quinazolin-2-yl)acetamide 5.4 g (0.022 mole) of 2-[1-(hydroxyimino)ethyl]-pyrazolo[1,5-c]quinazolin-5(6H)-one is suspended in 135 g of polyphosphoric acid and heated to a temperature of ~135° (oil bath temperature) for 10 minutes, under nitrogen, with mechanical stirring. The reaction mixture is poured onto 1.2 l of ice-water and stirred for 1 hour. The precipitates are filtered off, washed with water and dried overnight in vacuo at 75°. Yield: 5.35 g; 99% yield.

This crude product is combined with 1.2 g of similar material, dissolved in a mixture of methanol (1.5 l.) and chloroform (750 ml) and impregnated onto a small amount of silica gel. The product is chromatographed on a column (silica gel; 200 g) eluting the column successively with chloroform (1.0 l.), CHCl$_3$:MeOH (9:1; 6.0 l.) and CHCl$_3$:MeOH (6:1; 3.0 l.). The fractions containing the product (Rf 0.44) are combined and concentrated to a volume of ~250 ml. The fluffy white precipitates (1.4 g) that form are filtered off and dried for 24 hours in vacuo at 125° and re-dried once more in vacuo at 110° for 72 hours, m.p. 378°–380°.

EXAMPLES 93–104

Following the procedure of Example 91, but substituting the compounds indicated in Column I, Table V below for 1-acetylpyrazolo[1,5-c]quinazolin-5(6H)-one in Example 120, the compounds indicated in Column II are obtained.

TABLE V

| | Column I | | | | | Column II | | | | |
|---|---|---|---|---|---|---|---|---|---|---|
| Ex. No. | R⁴ (position) | R⁵ (position) | $R^3$ | $R^1$ | $R^2$ | R⁴ (position) | R⁵ (position) | $R^3$ | $R^1$ | $R^2$ |
| 93. | H | H | H | $CH_3$ | $\overset{O}{\underset{\|}{C}}CH_2CH_3$ | as in Column I | | | $CH_3$ | $\overset{NOH}{\underset{\|}{-C}}CH_2CH_3$ |
| 94. | H | H | H | $\overset{O}{\underset{\|}{CH_3C}}$ | ⬡ | | | | $\overset{NOH}{\underset{\|}{CH_3C-}}$ | ⬡ |
| 95. | H | H | H | H | $\overset{O}{\underset{\|}{C}}-\overset{}{\underset{CH_3}{C}}HCH_3$ | | | | H | $\overset{NOH}{\underset{\|}{-C}}\overset{}{\underset{CH_3}{C}}HCH_3$ |
| 96. | $CH_3(8)$ | H | $CH_3$ | H | $\overset{O}{\underset{\|}{C}}CH_3$ | | | | H | $\overset{NOH}{\underset{\|}{-C}}CH_3$ |
| 97. | $C_2H_5(8)$ | $C_2H_5(9)$ | H | H | $\overset{O}{\underset{\|}{C}}CH_3$ | | | | H | $\overset{NOH}{\underset{\|}{-C}}CH_3$ |
| 98. | Cl(9) | H | $CH_2$-⬡ | H | $\overset{O}{\underset{\|}{C}}CH_3$ | | | | H | $\overset{NOH}{\underset{\|}{-C}}CH_3$ |
| 99. | $CF_3(7)$ | H | ⬡ | H | $\overset{O}{\underset{\|}{C}}CH_3$ | | | | H | $\overset{NOH}{\underset{\|}{-C}}CH_3$ |
| 100. | $CH_3O(10)$ | H | H | H | $\overset{O}{\underset{\|}{C}}CH_3$ | | | | H | $\overset{NOH}{\underset{\|}{-C}}CH_3$ |
| 101. | $CH_3O(10)$ | H | $CH_2$-⬡-Cl | H | $\overset{O}{\underset{\|}{C}}CH_2CH_3$ | | | | H | $\overset{NOH}{\underset{\|}{-C}}CH_{3\,3}$ |
| 102. | $CH_3O(9)$ | H | H | $\overset{O}{\underset{\|}{CH_3C}}$ | $n-C_4H_9$ | | | | $\overset{NOH}{\underset{\|}{CH_3C-}}$ | $n-C_4H_9$ |
| 103. | H | H | $CH_2$-⬡-Cl | $\overset{O}{\underset{\|}{CH_3C}}$ | $i-C_3H_7$ | | | | $\overset{NOH}{\underset{\|}{CH_3C-}}$ | $i-C_3H_7$ |
| 104. | $CH_3O(10)$ | H | H | $\overset{O}{\underset{\|}{CH_3C}}$ | $\overset{O}{\underset{\|}{C}}CH_3$ | | | | $\overset{NOH}{\underset{\|}{CH_3C-}}$ | $\overset{}{\underset{\|}{C}}CH_3$ |

EXAMPLES 105–116

Following the procedure of Example 92 but substituting the compounds indicated in Column I, Table VI below for 2-(hydroxyiminoethyl)pyrazolo[1,5-c]quinazolin-5(6H)-one in Example 92, the compounds indicated in Column II below are obtained.

TABLE VI

| | | Column I | | | | | Column II | | |
|---|---|---|---|---|---|---|---|---|---|
| Ex. No. | R⁴ (position) | R⁵ (position) | R³ | R¹ | R² | R⁴ (position) R⁵ (position) R³ as in Column I | | R¹ | R² |
| 105. | H | H | H | $CH_3$ | $\underset{-CCH_2CH_3}{\overset{NOH}{\|}}$ | | | $CH_3$ | $-NHCCH_3$ (C=O) |
| 106. | H | H | H | $\underset{CH_3C-}{\overset{NOH}{\|}}$ | cyclohexyl | | | $CH_3CNH-$ (C=O) | cyclohexyl |
| 107. | H | H | H | H | $\underset{\underset{CH_3}{\|}}{\overset{NOH}{\underset{-CCHCH_3}{\|}}}$ | | | H | $\underset{\underset{CH_3}{\|}}{\overset{O}{\underset{-CCHCH_3}{\|}}}$ |
| 108. | $CH_3(8)$ | H | $CH_3$ | H | $\overset{NOH}{\underset{-CCH_3}{\|}}$ | | | H | $\overset{O}{-NHCCH_3}$ |
| 109. | $C_2H_5(8)$ | $C_2H_5(8)$ | H | H | $\overset{NOH}{\underset{-CCH_3}{\|}}$ | | | H | $\overset{O}{-NHCCH_3}$ |
| 110. | Cl(9) | H | $-CH_2-$phenyl | H | $\overset{NOH}{\underset{-CCH_3}{\|}}$ | | | H | $\overset{O}{-NHCCH_3}$ |
| 111. | $CF_3(7)$ | H | $-CH_2-$phenyl | H | $\overset{NOH}{\underset{-CCH_3}{\|}}$ | | | H | $\overset{O}{-NHCCH_3}$ |
| 112. | $CH_3O(10)$ | H | H | H | $\overset{NOH}{\underset{-CCH_3}{\|}}$ | | | H | $\overset{O}{-NHCCH_3}$ |
| 113. | $CH_3O(10)$ | H | $-CH_2-$(4-Cl-phenyl) | H | $\overset{O}{-CCH_3}$ | | | H | $\overset{O}{-NHCCH_3}$ |
| 114. | $CH_3O(9)$ | H | H | $\underset{CH_3C-}{\overset{NOH}{\|}}$ | $n-C_4H_9$ | | | $\overset{O}{CH_3CNH-}$ | $n-C_4H_9$ |
| 115. | H | H | $-CH_2-$(2-Cl-phenyl) | $\underset{CH_3C-}{\overset{NOH}{\|}}$ | $i-C_3H_7$ | | | $\overset{O}{CH_3CNH-}$ | $i-C_3H_7$ |
| 116. | $CH_3O(10)$ | H | H | $\underset{CH_3C-}{\overset{NOH}{\|}}$ | $\overset{NOH}{\underset{-CCH_3}{\|}}$ | | | $\overset{O}{CH_3CNH-}$ | $\overset{O}{-NHCCH_3}$ |

EXAMPLES 117–128

Following the procedure of Examples 7–8 but substituting the compounds indicated in Column I, Table VII below for N-(5,6-dihydro-5-oxopyrazolo[1,5-c]quinazolin-2-yl)acetamide in Example 7–8, the compounds indicated in Column II below are obtained.

TABLE VII

| | | Column I | | | | Column II | | | |
|---|---|---|---|---|---|---|---|---|---|
| Ex. No. | R⁴ (position) | R⁵ (position) | R³ | R¹ | R² | R⁴ (position) | R⁵ (position) R³ | R¹ | R² |
| 117. | H | H | H | $CH_3-$ | $-NHCOCH_3$ | as in Column I | | $CH_3$ | $NH_2$ |
| 118. | H | H | H | $CH_3CONH-$ | (cyclohexyl) | | | $NH_2$ | (cyclohexyl) |
| 119. | H | H | H | H | $-NHCOCH(CH_3)CH_3$ | | | H | $NH_2$ |
| 120. | $CH_3$(8) | H | $CH_3$ | H | $-NHCOCH_3$ | | | H | $NH_2$ |
| 121. | $C_2H_5$(8) | $C_2H_5$(8) | H | H | $-NHCOCH$ | | | H | $NH_2$ |
| 122. | Cl(9) | H | $CH_2$-(phenyl) | H | $-NHCOCH_3$ | | | H | $NH_2$ |
| 123. | $CF_3$(7) | H | (phenyl) | H | $-NHCOCH_3$ | | | H | $NH_2$ |
| 124. | $CH_3O$(10) | H | H | H | $-NHCOCH_3$ | | | H | $NH_2$ |
| 125. | $CH_3O$(10) | H | $CH_2$-(phenyl)-Cl | H | $-NHCOCH_3$ | | | H | $NH_2$ |
| 126. | $CH_3O$(9) | H | H | $CH_3CONH-$ | $n-C_4H_9$ | | | $NH_2$ | $n-C_4H_9$ |
| 127. | H | H | H | $CH_3CONH-$ ($CH_2$-(phenyl)-Cl) | $i-C_3H_7$ | | | $NH_2$ | $i-C_3H_7$ |
| 128. | $CH_3O$(10) | H | H | $CH_3CONH-$ | $-NHCOCH_3$ | | | $NH_2$ | $NH_2$ |

What is claimed is:
1. Compounds of the structure

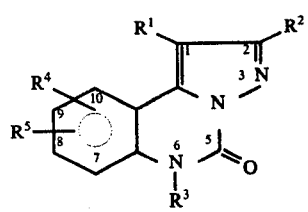

wherein R¹ is hydrogen, alkyl of 1 to 3 carbons, 1-(hydroxyimino)alkyl, alkanoylamino, amino, or

R² is 1-(hydroxyimino)alkyl, alkanoylamino, amino,

hydrogen, lower alkyl, phenyl or phenyl substituted by a single R⁴, the alkyl moiety present in the above R¹ and R² groups having 1 to 8 carbons;

R³ is hydrogen, lower alkyl having 1 to 8 carbons, benzyl, phenyl, phenyl substituted by a single R⁴ radical, dialkylaminoalkyl having 1 to 8 carbons in each of the alkyl groups, mono-hydroxyalkyl,

(wherein $R^6$ is hydrogen or alkyl, and $R^7$ is alkyl of 1 to 4 carbons), with the proviso that $R^1$ or $R^2$ is 1-(hydroxyimino)alkyl, alkanoylamino, or amino, when $R^3$ is hydrogen, lower alkyl having 1 to 8 carbons, benzyl or phenyl;

$R^4$ and $R^5$ may be the same or different and are hydrogen, lower alkyl of 1 to 4 carbons, lower alkoxy of 1 to 4 carbons, hydroxy, alkanoyloxy of 2 to 5 carbons,

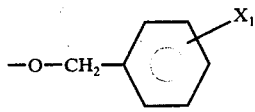

(wherein $X_1$ is hydrogen, lower alkoxy of 1 to 4 carbons), hydroxy, Cl, F, Br, $CF_3$ or $NO_2$, and physiologically acceptable salts thereof.

2. The compound of claim 1 wherein $R^1$ or $R^2$ is $NH_2$.

3. The compound of claim 1 wherein $R^1$ or $R^2$ is 1-(hydroxyimino)alkyl.

4. The compound of claim 1 wherein $R^1$ or $R^2$ is alkanoylamino.

5. The compound of claim 1 wherein $R^2$ is

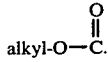

6. The compound of claim 1 wherein $R^3$ is hydrogen, lower alkyl, benzyl or phenyl and $R^1$ or $R^2$ is 1-(hydroxyimino)alkyl, aminoalkanoyl, or amino.

7. The compound of claim 1 wherein $R^3$ is dialkylaminoalkyl, hydroxyalkyl,

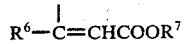

wherein $R^6$ is hydrogen, and $R^7$ is alkyl.

8. The compound of claim 7 wherein $R^1$ is hydrogen or lower alkyl.

9. The compound of claim 1 wherein $R^3$, $R^4$ and $R^5$ are hydrogen.

10. The compound of claim 1 having the name 6-[2-(dimethylamino)ethyl]pyrazolo[1,5-c]quinazolin-5(6H)-one and physiologically acceptable salts thereof.

11. The compound of claim 1 having the name 6-[3-(dimethylamino)propyl]pyrazolo[1,5-c]quinazolin-5(6H)-one and physiologically acceptable salts thereof.

12. The compound of claim 1 having the name 6-(3-hydroxypropyl)pyrazolo[1,5-c]quinazolin-5(6H)-one.

13. The compound of claim 1 having the name cis-8-chloro-6-(3-ethoxy-3-oxo-1-propenyl)-5,6-dihydro-5-oxo-pyrazolo[1,5-c]quinazoline-2-carboxylic acid ethyl ester.

14. The compound of claim 1 having the name 2-aminopyrazolo[1,5-c]quinazolin-5(6H)-one.

15. The compound of claim 1 having the name 6-(3-ethoxy-3-oxo-1-propenyl)-9-methoxy-5,6-dihydro-5-oxopyrazolo[1,5-c]quinazoline-2-carboxylic acid, ethyl ester.

16. The compound of claim 1 having the name 2-[1-(hydroxyimino)ethyl]pyrazolo[1,5-c]quinazolin-5(6H)-one.

17. The compound of claim 1 having the name N-(5,6-dihydro-5-oxopyrazolo[1,5-c]quinazolin-2-yl)acetamide.

18. A pharmaceutical composition for use in treating allergic conditions comprising a therapeutic amount of a compound as defined in claim 1 and a pharmaceutically acceptable carrier therefor.

19. A method for treating allergic conditions in mammals, which comprises administering to the mammalian host a therapeutic amount of a compound as defined in claim 1.

* * * * *

UNITED STATES PATENT AND TRADEMARK OFFICE
CERTIFICATE OF CORRECTION

PATENT NO. : 4,112,098

DATED : September 5, 1978

INVENTOR(S) : B. Richard Vogt

It is certified that error appears in the above-identified patent and that said Letters Patent are hereby corrected as shown below:

In structures,
> Column 1, structure I
> Column 1, structure at line 50
> Column 2, structure (Ia)
> Column 2, structure (Ib)
> Column 2, structure (Ic)
> Column 2, structure I
> Column 3, structure II
> Column 3, structure I'
> Column 4, structure at line 50
> Column 7, structure (Ic')
> Column 7, structure VI
> Column 8, structure VIII
> Column 8, structure VI
> Column 8, structure XII
> Column 8, structure XI
> Column 9, structure XIII
> Column 9, structure XIV
> Column 9, structure XV
> Column 9, structure XVI
> Table I, in the heading, structures in Columns I and III
> Ex. 17, Column II, $R_1$
> Table I-continued, in the heading, structures in Columns I and III
> Ex. 30, Column II, Z
> Table II, in the heading, structures in Columns I and IV
> Ex. 38, Column III, $R_3$
> Ex. 39, Column III, $R_3$
> Ex. 40, Column III, $R_3$ the ◯ in the six-membered ring representing three sets of double bonds should be a solid, legible circle.

UNITED STATES PATENT AND TRADEMARK OFFICE
CERTIFICATE OF CORRECTION

PATENT NO. : 4,112,098

DATED : September 5, 1978

INVENTOR(S) : B. Richard Vogt

It is certified that error appears in the above-identified patent and that said Letters Patent are hereby corrected as shown below:

In structures,

Ex. 41, Column III, $R_3$

Table II-continued, in the heading, structures in Columns I and IV

Ex. 51, Column II, Z

Table III, in the heading, structures in Columns I and II

Ex. 59, Column I, $R_3$

Ex. 60, Column I, $R_3$

Ex. 61, Column I, $R_3$

Ex. 62, Column I, $R_3$

Table III-continued, in the heading, structures in Columns I and II

Ex. 72, Column I, Z

Table IV, in the heading, structures in Columns I and III

Ex. 75, Column II, $R_3$

Ex. 76, Column II, $R_3$

Ex. 78, Column II, $R_3$

Ex. 79, Column II, $R_3$

Ex. 80, Column II, $R_3$

Ex. 81, Column II, $R_3$

Table IV-continued, in the heading, structures in Columns I and III

Ex. 83, Column II, $R_3$

Ex. 84, Column II, $R_3$ the ◯ in the six-membered ring representing three sets of double bonds should be a solid, legible circle.

UNITED STATES PATENT AND TRADEMARK OFFICE
CERTIFICATE OF CORRECTION

PATENT NO. : 4,112,098        Page 3 of 5

DATED : September 5, 1978

INVENTOR(S) : B. Richard Vogt

It is certified that error appears in the above-identified patent and that said Letters Patent are hereby corrected as shown below:

In structures,
  Ex. 86, Column II, $R_3$
  Ex. 87, Column II, $R_3$
  Ex. 88, Column II, $R_3$
  Ex. 90, Column II, $R_3$
  Table V, in the heading, structures in Columns I and II
  Ex. 94, Column I, $R^2$
  Ex. 94, Column II, $R^2$
  Ex. 98, Column I, $R^3$
  Ex. 99, Column I, $R^3$
  Ex. 101, Column I, $R^3$
  Ex. 103, Column I, $R^3$
  Table VI, in the heading, structures in Columns I and II
  Ex. 106, Column I, $R^2$
  Ex. 106, Column II, $R^2$
  Ex. 110, Column I, $R^3$
  Ex. 111, Column I, $R^3$
  Ex. 113, Column I, $R^3$
  Ex. 115, Column I, $R^3$
  Ex. 118, Column I, $R^2$
  Ex. 118, Column II, $R^2$
  Ex. 122, Column I, $R^3$ the  in the six-membered ring representing three sets of double bonds should be a solid, legible circle.

UNITED STATES PATENT AND TRADEMARK OFFICE
CERTIFICATE OF CORRECTION

PATENT NO. : 4,112,098
DATED : September 5, 1978
INVENTOR(S) : B. Richard Vogt

It is certified that error appears in the above-identified patent and that said Letters Patent are hereby corrected as shown below:

In structures,
  Ex. 123, Column I, $R^3$
  Ex. 125, Column I, $R^3$
  Ex. 127, Column I, $R^3$
  Claim 1, first structure and last structure,
the ◯ in the six-membered ring representing three sets of double bonds should be a solid, legible circle.

Column 1, line 31, insert --(-- before "optionally".
Column 1, line 64, "or" should read --and--.
Column 3, in the reaction scheme, formula III should read
  --$R^1=C\equiv C-R^2$--.
Column 4, line 3, "now" should read --not--.
Column 4, line 12, "abovede-" should read --above-de- --.
Column 4, line 16, "abovedescribed" should read --above-described--.
Columns 22 and 24, in Table IV and Table IV-continued, the structure in Column III should read -- 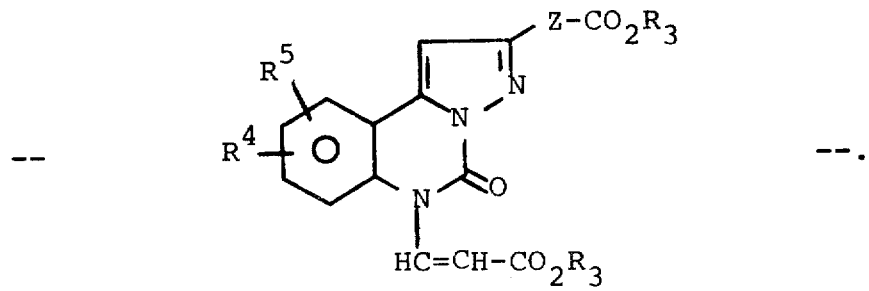 --.

UNITED STATES PATENT AND TRADEMARK OFFICE
CERTIFICATE OF CORRECTION

PATENT NO. : 4,112,098

DATED : September 5, 1978

INVENTOR(S) : B. Richard Vogt

It is certified that error appears in the above-identified patent and that said Letters Patent are hereby corrected as shown below:

Ex. 104, Column II, $R^2$, should read -- $-\overset{\text{NOH}}{\underset{\|}{C}}CH_3$ --.

Ex. 107, Column II, $R^2$, should read -- $-NH\overset{O}{\underset{\|}{C}}\underset{\underset{CH_3}{|}}{CH}CH_3$ --.

Ex. 113, Column I, $R^2$, should read -- $-\overset{\text{NOH}}{\underset{\|}{C}}CH_3$ --.

Ex. 121, Column I, $R^2$, should read -- $-NH\overset{O}{\underset{\|}{C}}CH_3$ --.

Column 30, line 65, after "$R^4$", insert --substituent--.

Signed and Sealed this

Twenty-second Day of May 1979

[SEAL]

Attest:

RUTH C. MASON
Attesting Officer

DONALD W. BANNER
Commissioner of Patents and Trademarks